US008351679B2

(12) United States Patent
Fukami

(10) Patent No.: US 8,351,679 B2
(45) Date of Patent: Jan. 8, 2013

(54) EXCLUSION OF RECOGNIZED PARTS FROM INSPECTION OF A CYLINDRICAL OBJECT

(75) Inventor: Yukiko Fukami, Kanagawa (JP)

(73) Assignee: Kirin Techno-System Company, Limited, Kanagawa (JP)

( * ) Notice: Subject to any disclaimer, the term of this patent is extended or adjusted under 35 U.S.C. 154(b) by 1062 days.

(21) Appl. No.: 12/300,823

(22) PCT Filed: May 16, 2007

(86) PCT No.: PCT/JP2007/060041
§ 371 (c)(1),
(2), (4) Date: Dec. 11, 2008

(87) PCT Pub. No.: WO2007/135915
PCT Pub. Date: Nov. 29, 2007

(65) Prior Publication Data
US 2009/0148031 A1    Jun. 11, 2009

(30) Foreign Application Priority Data

May 23, 2006   (JP) .................. 2006-143181
Sep. 25, 2006  (JP) .................. 2006-258263

(51) Int. Cl.
*G06K 9/00*   (2006.01)
*G01N 21/00*  (2006.01)
*H04N 7/18*   (2006.01)
(52) U.S. Cl. ............... 382/141; 356/241.1; 348/130; 382/152
(58) Field of Classification Search ............. None
See application file for complete search history.

(56) References Cited

U.S. PATENT DOCUMENTS 4,079,416 A * 3/1978 Faani et al. ........... 348/130
(Continued)

FOREIGN PATENT DOCUMENTS
JP        50158387      12/1975
(Continued)

OTHER PUBLICATIONS

Supplementary European Search Report dated Jan. 24, 2012 issued in corresponding European Patent Application No. 07743476.9.

*Primary Examiner* — Barry Drennan
(74) *Attorney, Agent, or Firm* — Sughrue Mion, PLLC

(57) ABSTRACT

A surface inspection apparatus, which includes a detecting device of scanning a surface of an inspection object with an inspection light and outputting a signal corresponding to a light amount of refection light from the surface, generates a two-dimensional image of the surface of the inspection object on the basis of the output signal of the detecting device (S1), classifies pixels contained in the two-dimensional image into a first group of pixels having tones corresponding to defects on the surface of the inspection object and a second group of pixels having tones not corresponding to the defects, extracts the first group of pixels as a defect candidate part for each region surrounded by second groups of pixels (S3 to S5), discriminates a defect candidate part larger than a prescribed size as a defect (S6), inspects the two-dimensional image for each specific inspection region, and identifies an inspection region as a defect region, in which density of defect candidate parts that are smaller than the prescribed size is equal to or more than a prescribed level (S7, S8).

5 Claims, 13 Drawing Sheets

U.S. PATENT DOCUMENTS

| | | | |
|---|---|---|---|
| 4,691,231 A * | 9/1987 | Fitzmorris et al. | 348/127 |
| 5,321,767 A * | 6/1994 | Murase | 382/149 |
| 7,602,487 B2 * | 10/2009 | Fukami et al. | 356/241.1 |
| 2003/0223631 A1 | 12/2003 | Ine | |
| 2004/0032979 A1 | 2/2004 | Honda et al. | |
| 2006/0159330 A1 * | 7/2006 | Sakai et al. | 382/141 |
| 2007/0132990 A1 * | 6/2007 | Fukami et al. | 356/241.1 |
| 2009/0010527 A1 | 1/2009 | Honda et al. | |
| 2009/0074286 A1 * | 3/2009 | Kitazawa et al. | 382/144 |

FOREIGN PATENT DOCUMENTS

| | | |
|---|---|---|
| JP | 08101130 | 4/1996 |
| JP | 11211674 | 8/1999 |
| JP | 11281582 | 10/1999 |
| JP | 11326226 | 11/1999 |

\* cited by examiner

FIG. 7

|   | 2 |   |   |   | 1 |   |   |   |
|---|---|---|---|---|---|---|---|---|
|   | 2 |   |   |   | 1 | 1 | 1 |   |
| 2 | 2 |   |   |   |   |   | 1 |   |

210 (LABEL No. 2)  210 (LABEL No. 1)

FIG.12

| y1 | Data of Reference Image 411 | N1 |
|---|---|---|
| y2 | Data of Reference Image 412 | N2 |

EXCLUSION OF RECOGNIZED PARTS FROM INSPECTION OF A CYLINDRICAL OBJECT

CROSS-REFERENCE TO PRIOR APPLICATION

This is the U.S. National Phase Application under 35 U.S.C. §371 of International Patent Application No. PCT/JP2007/060041 filed May 16, 2007, which claims the benefit of Japanese Patent Application Nos. 2006-143181 filed May 23, 2006, 2006-258263 filed Sep. 25, 2006, all of them are incorporated by reference herein. The International Application was published in Japanese on Nov. 29, 2007 as WO2007/135915 a1 under pct article 21(2).

TECHNICAL FIELD

The present invention relates to a surface inspection apparatus which scans the surface of an inspection object with an inspection light, receives the reflection light from the surface, and detects defects of the surface of the inspection object on the basis of the light amount of the reflection light, or which takes the image of the surface of the inspection object, obtains the two-dimensional image thereof, and discriminates the existence or nonexistence of defects on the basis of the density value of the pixels in the two-dimensional image.

RELATED ART

As an apparatus which inspects the inner peripheral surface of a cylindrical inspection object, a surface inspection apparatus is known, which feeds out a hollow shaft-like inspection head in the axial direction of the inspection head while rotating the inspection head around its axis so as to be inserted into the interior of the inspection object, irradiates the inspection light with a laser beam serving as an inspection light from the outer circumference of the inspection head, successively scans the inner peripheral surface of the inspection object from one end to the other end along the axial direction, receives the reflection light from the inspection object corresponding to the scanning through the inspection head, and discriminates the existence or nonexistence of defects in the inner circumferential surface on the basis of the light amount of the received reflection light (refer to Patent document 1, for example).
Patent document 1: JP11-A-281582

SUMMARY OF INVENTION

Problems to be Solved by the Invention

Since the above surface inspection apparatus utilizes a Laser beam as an inspection light, miniature defects can be detected By narrowing the illuminated area of the inspection light. However, when increasing a resolution of detectable defect more than necessary, even miniature asperities or the like which are not treated as defects in the visual inspection might be discriminated as defects, so that discrepancy might be caused between the inspection results by a visual inspection and the inspection using apparatus. In order to solve such inconveniences, it is effective to set a threshold level for the size of the defect in the target of inspection, and to treat only the ones beyond the threshold level as defects. However, when miniature asperities or the like, each of which alone is smaller than the threshold level, are concentrated in a relatively close area, the group of them might be identified as a bunch of defects in a view of a person for inspection.

On the other hand, each miniature asperity is distinctly compared in size with the threshold level in the surface inspection apparatus, and the apparatus will discriminate that all of them are not defects. Thus, assuming that the inspection result of a visual inspection is set as a criterion, this might be evaluated as overlook of defects, and the reliability of the inspection might be damaged.

Moreover, when a processed part such as a hole or a convexo-concave part on the inner circumferential surface of the inspection object exists in the above surface inspection apparatus, it becomes difficult to distinguish the processed part from defects; and the processed part may be erroneously identified as defects. In the case that defects are discriminated by using the density value distribution on the two-dimensional image of expanding the inner circumferential surface in a planar manner, if the position of the image of the processed part on the two-dimensional image is known, the erroneous decision can be avoided by eliminating the image of the processed part from the target of defect discrimination. Such processes are performed in general as masking processes in the field of image processing. However, even when the position of the image of the processed part in the axial direction of the cylindrical inner circumferential surface can be uniquely specified with reference to the edge or the like of the inner circumferential surface, no appropriate reference for specifying the position of the processed part exists in the circumference direction, and the position of the image of the processed part is varied in accordance with the positional relation between the scanning starting position and the processed part. Thus, simply by preparing a sheet of the mask image including the images of all processed parts existing on the inner circumferential surface and overlapping it on the image of the inner circumferential surface, the position of the mask might be shifted in the circumference direction with respect to the images of the processed parts, thereby affecting defect discrimination. Even when trying to match the position of the mask with the images of the processed parts by moving the mask image on the two-dimensional image, the data amount of the mask image in a size corresponding to the whole area of the inner circumferential surface is large, and it takes long time to process them.

It is an object of the present invention to provide a surface inspection apparatus which, when miniature asperities or the like, each of which alone is not detected as a defect, are closely concentrated in a relatively close region, can detect them as defects or semi-defects while eliminating the possibility that miniature asperities or the like on the surface of the inspection object might be detected singly as a defect. Moreover, it is another object of the present invention to provide a surface inspection apparatus which can perform accurate inspections by eliminating the influence of the processed part, which exists on the surface of the inspection object, on the discrimination of the existence or nonexistence of defects, and speed up the process.

Means for Solving Problem

The surface inspection apparatus according to an aspect of the present invention includes a detecting device which scans a surface of an inspection object with an inspection light, receives refection light from the surface, and outputs a signal corresponding to the light amount of the reflection light; an image generating device which generates a two-dimensional image of the surface of the inspection object on the basis of the output signal of the detecting device; a defect candidate extracting device which classifies pixels contained in the two-dimensional image into a first group of pixels having tones corresponding to defects on the surface of the inspection object and a second group of pixels having tones not corresponding to the defects, and extracts the first group of pixels as a defect candidate part for each region surrounded by second groups of pixels; a defect identifying device which discriminates, in defect candidate parts, a defect candidate part larger than a prescribed size as a defect; and a defect region identifying device which inspects the two-dimensional image for each specific inspection region, and identifies an inspection region, in which density of defect candidate parts that are smaller than the prescribed size is equal to or more than a prescribed level, as a defect region. Thus, the above problems are solved.

According to the above surface inspection apparatus, a two-dimensional image of a tone distribution corresponding to the light amount of the reflection light from the surface of the inspection object is generated by the image generating device. The pixels contained in the two-dimensional image are classified into a first group of pixels having tones corresponding to defects and a second group of pixels having tones not corresponding to the defect. Furthermore, by extracting the first group of pixels as a defect candidate part for each region surrounded by second group of pixels, each individual defect existing on the surface of the inspection object can be specified on the two-dimensional image as a defect candidate part. Then, each defect candidate part that is equal to or larger than a prescribed size is identified as a defect. On the other hand, when relatively small defect candidate parts, each of which alone is not identified as a defect, are closely concentrated in an inspection region equally or more than a prescribed level, the inspection region is identified as a defect region. Thus, when miniature asperities or the like, each of which alone is not detected as a defect, are closely concentrated in a relatively close region, the closely concentrated region can be identified as a defect region; and the defect region can be detected as a defect or a semi-defective region and can be presented to a user of the apparatus, while eliminating the possibility that each of miniature asperities or the like alone on the surface of the inspection object might be detected as a defect.

In an aspect of the present invention, the defect candidate extracting device may extract the defect candidate part by performing a labeling process on the first group of pixels contained in the two-dimensional image. The labeling process is known as a technique of grouping a group of pixels contained in a two-dimensional image by using their tones as a key. By utilizing the labeling process, a first group of pixels having tones corresponding to defects can be extracted for each region surrounded by second group of pixels from the two-dimensional image of the surface of the inspection object, as a defect candidate part.

In an aspect of the present invention, the defect region identifying device may discriminate the density on the basis of at least any one of areas and the number of the defect candidate parts in the inspection region, which are smaller than the prescribed size. Since the density of the miniature defect candidate parts in the inspection region correlates with the number or the areas of the defect candidate parts, the density thereof can be discriminated appropriately with reference to at least one of the number or the areas.

In an aspect of the present invention, the defect region identifying device may discriminate that the density is equal to or more than the prescribed level when the number of defect candidate parts in the inspection region, which are smaller than the prescribed size and which are equal to or larger than a prescribed area, is equal to or larger than a prescribed value. By using such a discriminating criterion, the degree of coincidence between the inspection tendency of a person for inspection with regard to the closely concentrated part such as miniature asperities and the inspection tendency of defect regions by a surface inspection apparatus can be improved.

In an aspect of the present invention, the surface inspection apparatus may further include a position calculating device which calculates a position of a gravity center of a group of defect candidate parts that are contained in the inspection region identified as the defect region as a position representing the group of defect candidate parts in the inspection region. It is highly possible that the closely concentrated part of the miniature defect candidate parts is seen as a bunch of defects in a visual observation of a person for inspection. Accordingly, by calculating the position of the gravity center as a position representing these defect candidate parts in stead of the individual positions of the defect candidate parts, the position of the closely concentrated part of the defect candidate parts can be presented more properly to a person for inspection.

The surface inspection apparatus according to another aspect of the present invention obtains a two-dimensional image of expanding a cylindrical surface of an inspection object in a planar manner, and discriminates existence or nonexistence of a defect on the surface on the basis of density values of pixels in the two-dimensional image, the surface inspection apparatus, and includes a reference image storing device which stores images of processed parts to be appeared on the two-dimensional image corresponding to processed parts existing on the surface as separate reference images for each of processed parts which are different in at least shapes or sizes, and stores a position of each image of each processed part in an axis-equivalent direction equivalent to an axial direction of the surface and the number of each of images of a same processed part which should exist in a circumference-equivalent direction equivalent to a circumference direction of the surface in a correlated manner with each of the reference images; and a defect discriminating device which specifies a region to be eliminated from a target of defect discrimination on the two-dimensional image on the basis of each reference image and the position and the number correlated with each reference image, and discriminates the existence or nonexistence of the defect on the basis of the density values of pixels outside the specified region. Thus, the above problems are solved.

According to the above surface inspection apparatus, a separate reference image is prepared for each of the processed parts, in which shapes, sizes, or both of them are different from each other. Thus, the size of each reference image is remarkably reduced in comparison to the case of preparing a reference image in a size corresponding to the entire surface, and the data amount thereof becomes significantly small. Moreover, the position of the image of the processed part in the axis-equivalent direction on the two-dimensional image is stored in a correlated manner with the reference image. Thus, when one wants to eliminate the image of the specific processed part from the target of defect discrimination, the region where the image of the processed part can exist can be narrowed to a part of the region in the axis-equivalent direction of the two-dimensional image by using the position relating to the image of the specific processed part in the axis-equivalent direction as a key. Then it may be discriminated whether an image coinciding with a reference image exists by comparing the density value distributions of the reference image and the two-dimensional image within the narrowed region, and the region where the coincided image exist may be eliminated from the target of defect discrimination. Thus, it is not necessary to compare the reference image with the whole surface of the two-dimensional image. Coupled with the above-mentioned reduction of the data amount of the reference image, the process can be sped up. Furthermore, the number of images of a same processed part which should exist in a circumference-equivalent direction of the two-dimensional image is stored in a correlated manner with the reference image. Thus, the possibility that more number of the regions than the number of processed parts might be erroneously discriminated from the narrowed region on the two-dimensional image as the regions to be eliminated from the target of defect discrimination can be eliminated. In this way, the occurrence of the inspection error of looking over defects even when the defects exist can be prevented. Accordingly, an accurate inspection can be preformed by eliminating the influence of the processed part existing on the surface of the inspection object on the discrimination of the existence or nonexistence of defects.

In another aspect of the present invention, the defect discriminating device may includes an eliminating region specifying device (60), which narrows a region to be compared with the reference image on the two-dimensional image to a part of the two-dimensional image in the axis-equivalent direction with reference to the position correlated with the reference image, compares density values of pixels of the reference image and of the two-dimensional image in the narrowed region, and specifies the same number of regions as the number correlated with the reference image as regions to be eliminated from the target of defect discrimination on the basis of the comparison result. In this aspect, the density values of the reference image and the two-dimensional image are compared in the region narrowed with reference to the position correlated with the reference image. Accordingly, the process is sped up than in a case of sequentially comparing the entire surface of the two-dimensional image with the reference image. Furthermore, the number of regions to be eliminated from the target of defect discrimination is determined with reference to the number correlated with the reference image. Thus, the possibility that more numbers of the regions than the number of processed parts might be eliminated from the target of defect discrimination can be eliminated. For example, even when defects similar to a processed part exists together with a processed part in the circumference direction and even when the image of the defect is eliminated from the target of defect discrimination, any one of the images of the processed parts will remain as a target of defect discrimination. And thus, by alternatively discriminating the image of the processed part as a defect, the existence or nonexistence of defects is discriminated correctly.

Furthermore, the eliminating region specifying device may discriminate a degree of coincidence between the reference image and an inspection target image having the same shape and size as those of the reference image on the two-dimensional image, with sequentially changing a position of the reference image in the narrowed region relatively with respect to the two-dimensional image in the circumference-equivalent direction, and, when the discriminated degree of coincidence exceeds a prescribed threshold level, specifies a region of the inspection target image as a region to be eliminated from the target of defect discrimination. In this case, the region to be eliminated from the target of defect discrimination can be specified by changing the position of the inspection target image in the axis-equivalent direction, while discriminating the degree of coincidence between the reference image having the same shape and size and the inspection target image, and by inspecting accurately and speedily in a partial region of the two-dimensional image narrowed on the basis of the position correlated with the reference image. The degree of coincidence may be calculated by normalized correlation between the reference image and the inspection target image. In this way, calculation of the degree of coincidence between the images and discrimination on the basis of the threshold level can be processed speedily.

In another aspect of the present invention, the reference image may correspond to an image obtained by extracting a minimum rectangle region required to enclose an image of a single processed part from the two-dimensional image. Accordingly, as much as the surroundings of the image of the processed part can be treated as the target of defect discrimination, while keeping the size of the reference image to a minimum require size.

Effect of Invention

According to the above surface inspection apparatus, among the defect candidate part extracted from the two-dimensional of the surface of the inspection object, the defect candidate parts that are equal to or larger than a prescribed size are identified as defects. On the other hand, when relatively small defect candidate parts, each of which alone is not identified as a defect, are closely concentrated in an inspection region equally or more than a prescribed level, the inspection region is identified as a defect region. Accordingly, while eliminating the possibility that miniature asperities or the like alone on the surface of the inspection object might be detected as a defect, when miniature asperities or the like, each of which singly is not detected as a defect, are closely concentrated in a relatively close region, the closely concentrated region can be identified as a defect region, and the defect region can be detected as a defect region or a semi-defective region, and can be presented to a user of the apparatus. In this way, the overlook of the region where miniature asperities or the like are closely concentrated can be prevented, the degree of coincidence between the inspection result of a visual observation of a user and the inspection result of a surface inspection apparatus can be improved, and the degradation of the reliability of the inspection using the surface inspection apparatus can be prevented. Moreover, the data amount of each reference image can be reduced by storing a separate reference image for each of the processed parts having different shapes or different size. The position of the image of the processed part in the axis-equivalent direction on the two-dimensional image is stored in a correlated manner with the reference image. Thus, when the region to be eliminated from the target of defect discrimination is specified, the region where the image of the processed part can exist, namely the region to be compared with the reference image, can be narrowed in a partial region in the axis-equivalent direction of the two-dimensional image, with reference to the position correlated to with the reference image. Coupled with the reduction of the data amount of the reference image, the process can be sped up. Furthermore, the number of images of a same processed part which should exist in a circumference-equivalent direction of the two-dimensional image is stored in a correlated manner with the reference image. Thus, the possibility that more number of the regions than the number of processed parts might be erroneously determined as an exempt region from the target of defect discrimination. Accordingly, an accurate inspection can be performed by eliminating the influence of the processed part existing on the surface of the inspection object on the discrimination of the existence or nonexistence of defects.

BRIEF DESCRIPTION OF DRAWINGS

Figure 7:
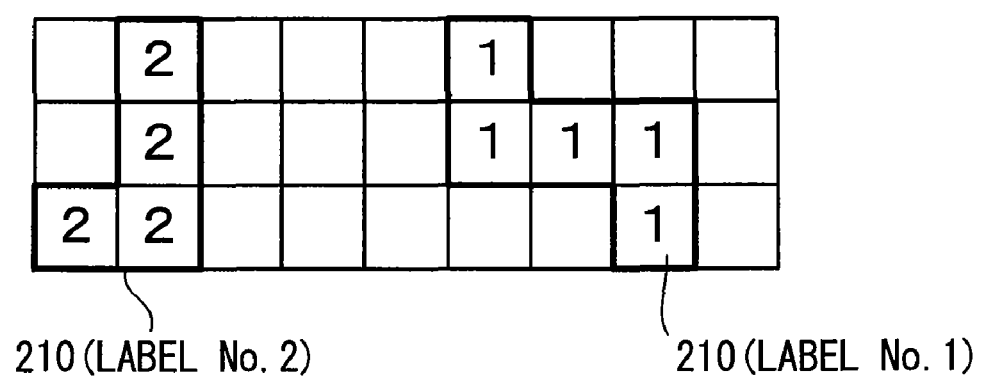

FIG. 7 is a view showing a state in which the label numbers added to the pixels of FIG. 6 are further organized.

FIG. 12 is a view showing the data structure of the reference image stored in the storage unit.

BEST MODE FOR CARRYING OUT THE INVENTION

Figure 1:
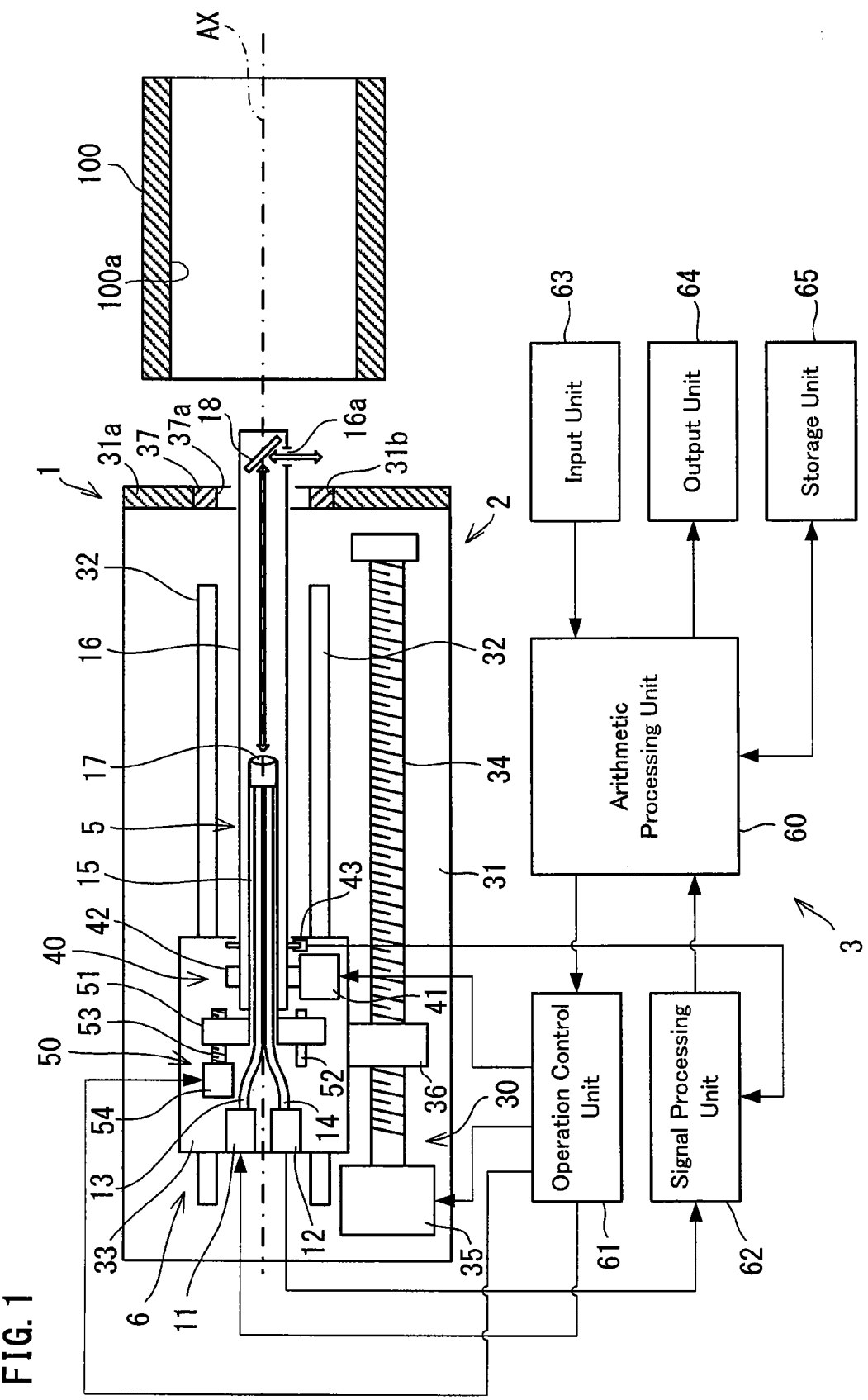
FIG. 1 is a view showing a schematic structure of a surface inspection apparatus in one embodiment of the present invention.

FIG. 1 shows a schematic configuration of a surface inspection apparatus according to one embodiment of the present invention. A surface inspection apparatus 1 is an apparatus that is adapted to the inspection of an inner circumferential surface 100a provided on an inspection object 100, and includes an inspection mechanism 2 for executing such inspection, and a control unit 3 for executing the operation control of the inspection mechanism 2 and the processing of measured results by the inspection mechanism 2 or the like. Furthermore, the inspection mechanism 2 includes a detection unit 5 serving as a detection device for projecting an inspection light to the inspection object 100 and for receiving a reflection light from the inspection object 100, and a drive unit 6 for making the detection unit 5 to work in a prescribed manner.

The detection unit 5 includes a laser diode (hereinbelow, called LD) 11 serving as the light source of the inspection light, and a photo detector (hereinbelow, called PD) 12 which receives the reflection light from the inspection object 100 and outputs a signal of electric current or electric voltage corresponding to the light amount of the reflection light per unit time (the intensity of the reflection light), a light projecting fiber 13 which guide the inspection light projected from the LD 11 toward the inspection object 100, a light receiving fiber 14 for guiding the reflection light from the inspection object 10 to PD12, a holding tube which holds these fibers 12, 14 in a bundled state, and a hollow shaft-like inspection head 16 disposed coaxially with the holding tube 15 outside thereof. The inspection head 16 is rotatably supported by bearings not shown in the drawing.

A lens 17 is disposed at the tip of the holding tube 15, which causes the inspection light, which is guided through the light projecting fiber 13, to emerge in a beam shape along the directions of an axis AX of the inspection head 16 (hereinbelow, called the axial directions) and condenses the reflection light propagating in the reverse direction of the inspection light along the axial direction of the inspection head 16 to the light receiving fiber 14. A mirror 18 serving as an optical path changing device is secured to at the tip part (the right end part in FIG. 1) of the inspection head 1, and a light transmission window 16a is disposed oppositely with the mirror 18 at the outer circumference of the inspection head 16. The mirror 18 changes the optical path of the reflection light incident from the light transmission window 16a into the interior of the inspection head 16 in the direction of propagating toward the lens 17.

The drive unit 6 includes a linear drive mechanism 30, a rotary drive mechanism 40, and a focus adjusting mechanism 50. The linear drive mechanism 30 is provided as a linear drive device for moving the inspection head 16 in the axial direction. In order to realize such a function, the linear drive mechanism 30 includes a base 31, a pair of rails 32 secured on the base 31, a slider 33 movable along the rail 32 in the axial direction of the inspection head 16, a lead screw 34 disposed at the side of the slider 33 in parallel with the axis AX of the inspection head 16, and an electric motor 35 of rotary driving the lead screw 34. The slider 33 functions as a device of supporting the entire detection unit 5. Namely, LD11 and PD12 are secured to the slider 33, the inspection head 16 is attached to the slider 33 via the rotary drive mechanism 40, and the holding tube 15 is attached to the slider 33 via the focus adjusting mechanism 50. Furthermore, a nut 36 is secured to the slider 33, and a lead screw 34 is screwed into the nut 36. Accordingly, by rotary driving the lead screw 34 by the electric motor 35, the slider 33 is moved along the rail 32 in the axial direction of the inspection head 16 and this is accompanied by the move of the entire detection unit 5 supported by the slider 33 in the axial direction of the inspection head 16. By the drive of the detection unit 5 using the linear drive mechanism 30, the illumination position (the scanning position) of the inspection light on the inner peripheral surface 100a of the inspection object 1 can be changed in the axial direction of the inspection head 16.

A wall part 31a is disposed at the front end (the right end in FIG. 1) of the base 31, and a through hole 31b coaxially with the inspection head 16 is provided to the wall part 31a. A sample piece 37 is attached to the through hole 31b. The sample piece 37 is provided as a sample for determining the operation condition of the surface inspection apparatus 1, and a through hole 27a coaxially with the inspection head 16 is provided on its centre line. The through hole 37a has an inner diameter at which the inspection head 16 can pass through, and the inspection head 16 goes through the through hole 37a and is fed out into the interior of the inspection object 100.

The rotary drive mechanism 40 is provided as a rotary drive device which rotates the inspection head 16 around the axis AX. In order to realize such a function, the rotary drive mechanism 40 includes an electric motor 41 serving as a rotary drive source and a transmission mechanism 42 of transmitting the rotation of the electric motor 41 to the inspection head 16. A commonly known rotation transmitting mechanism such as a belt transmitting device or a train of gears may be used for a transmission mechanism 42, but a belt transmitting device is used in this embodiment. By transmitting the rotation of the electric motor 41 to the inspection head 16 via the transmission mechanism 42, the inspection head 16 is rotated around the axis AX accompanied with the mirror 18 secured to thereinside. By the rotation of inspection head 16 using the rotary drive mechanism 40, the illumination position of the inspection object 100 can be changed in the circumferential direction of the inspection object 100. Moreover, by combining the move in the axial direction of the inspection head 16 with the rotation thereof around the axis AX, the inner peripheral surface 100a of the inspection object 100 can be scanned by the inspection light over the whole surface thereof. It is noted that the holding tube 15 does not rotate in the rotation of the inspection head 16. Furthermore, the rotary drive mechanism 40 is provided with a rotary encoder 43 which outputs a pulse signal every time the inspection head 16 is rotated by a prescribed unit angle. The number of pulse signals outputted from the rotary encoder 43 is correlated with the rotation amount (the rotation angle) of the inspection head 16, and the cycle of the pulse signals is correlated with the rotation speed of the inspection head 16.

The focus adjusting mechanism 50 is provided as a focus adjusting device which drives the holding tube 15 in the direction of the axis AX in such a manner that the inspection light focuses on the inner peripheral surface 100a of the inspection object 100. In order to realize such a function, the focus adjusting mechanism 50 includes a supporting plate 51 secured to the base end of the holding tube 15, a rail 52 disposed between the slider 33 of the linear drive mechanism 30 and the supporting plate 51 and of guiding the supporting plate 51 in the axial direction of the inspection head 16, a lead screw 53 disposed in parallel with the axis AX of the inspection head 16 and screwed into the supporting plate 51, and an electric motor 54 of rotary driving the lead screw 53. By rotary driving the lead screw 53 by the electric motor 54, the supporting plate 51 is moved along the rail 52, and the holding tube 15 is moved in the axial direction of the inspection head 16. In this way, the length of the optical path from the lens 17 to the inner peripheral surface 100a via the mirror 18 can be adjusted in a manner that the inspection light is focused on the inner peripheral surface 100a of the inspection object 100.

Next, the control unit 3 will be described. The control unit 3 includes an arithmetic processing unit 60 serving as a computer unit which performs management of the inspection process by the surface inspection apparatus 1, processing of measured result of the detection unit 5, and the like; an operation control unit 61 which controls the operation of the parts in the detection unit 5 in accordance with the instructions by the arithmetic processing unit 60; a signal processing unit 62 which executes a prescribed processing on the output signals of PD12; an input unit 63 for inputting a user's instructions to the arithmetic processing unit 60, and an output unit 64 for presenting the inspection result processed by the arithmetic processing unit 60 or the like to the user; and a storage unit 65 of storing a computer program to be executed in the arithmetic processing unit 60, measured data and the like. The arithmetic processing unit 60, the input unit 63, the output unit 64, and the storage unit 65 can be configured by utilizing a general purpose computer equipment such as a personal computer. In this case the input unit 63 is provided with input devices such as a keyboard and a mouse, and the output unit 64 is a monitor apparatus. The output device such as a printer may be added to the output unit 64. As the storage unit 65, a storage device such as a hard disk storage device or a semiconductor memory capable of keeping its content can be used. The operation control unit 61 and the signal processing unit 62 may be embodied either by a hardware control circuit(s) or a computer unit(s).

In the case of inspecting the surface of the inner peripheral surface 100a of the inspection object 100, the arithmetic processing unit 60, the operation control unit 61, and the signal processing unit 62 will be operated respectively in the following manner. It is noted that in this case the inspection object 100 is disposed coaxially with the inspection head 16. At the start of the inspection, the arithmetic processing unit 60 instructs the operation control unit 61 to start the necessary operation for inspecting the inner peripheral surface 100a of the inspection object 100 in accordance with the instructions from the input unit 63. The operation control unit 61, which receives the instruction, makes LD11 to radiate with a prescribed intensity and concurrently controls the operations of the motors 35 and 41 in such a manner that the inspection head 16 is moved in the axial direction and is rotated around the axis AX at a constant speed. Furthermore, the operation control unit 61 controls the operation of the motor 54 in such a manner that the inspection light focuses on the inner peripheral surface 100a serving as a surface to be inspected. By these controls of the operation, the inner peripheral surface 100a is scanned from one end to the other end thereof by the inspection light. It is noted as for driving out the inspection head 16 in the axial direction that the inspection head 16 may be fed out at a constant speed or moved intermittently with a prescribed pitch for every rotation of the inspection head 16.

Linked with that scanning of the inner peripheral surface 100a, the output signal of PD12 is successively conducted to the Signal processing unit 62. The signal processing unit 62A performs analog signal processing on the output signal of the PD 12A, which is needed for the arithmetic processing unit 60 to process that signal, subsequently performs A/D conversion of that processed analog signal with a prescribed bit depth, and outputs the obtained digital signal to the arithmetic processing unit 60 as a reflected light signal. Various processing's may be used appropriately for the signal processing executed by the arithmetic processing unit 60, including a processing of non-linearly amplifying the output signal so as to enlarge the difference in brightness-darkness of the reflection light detected by PD12, and a processing of removing noise components from the output signal. Fast Fourier transformation, Inverse Fourier transformation, or the like can be also combined appropriately. Moreover, the A/D conversion by the signal processing unit 62 is executed by utilizing the pulse trains outputted from the rotary encoder 43 as a sampling clock signal. In this way, a digital signal in a tone correlated with the light receiving amount of PD12 during the period while the inspection head 16 rotates by a prescribed angle is generated and is outputted from the signal processing unit 62.

Figure 2:
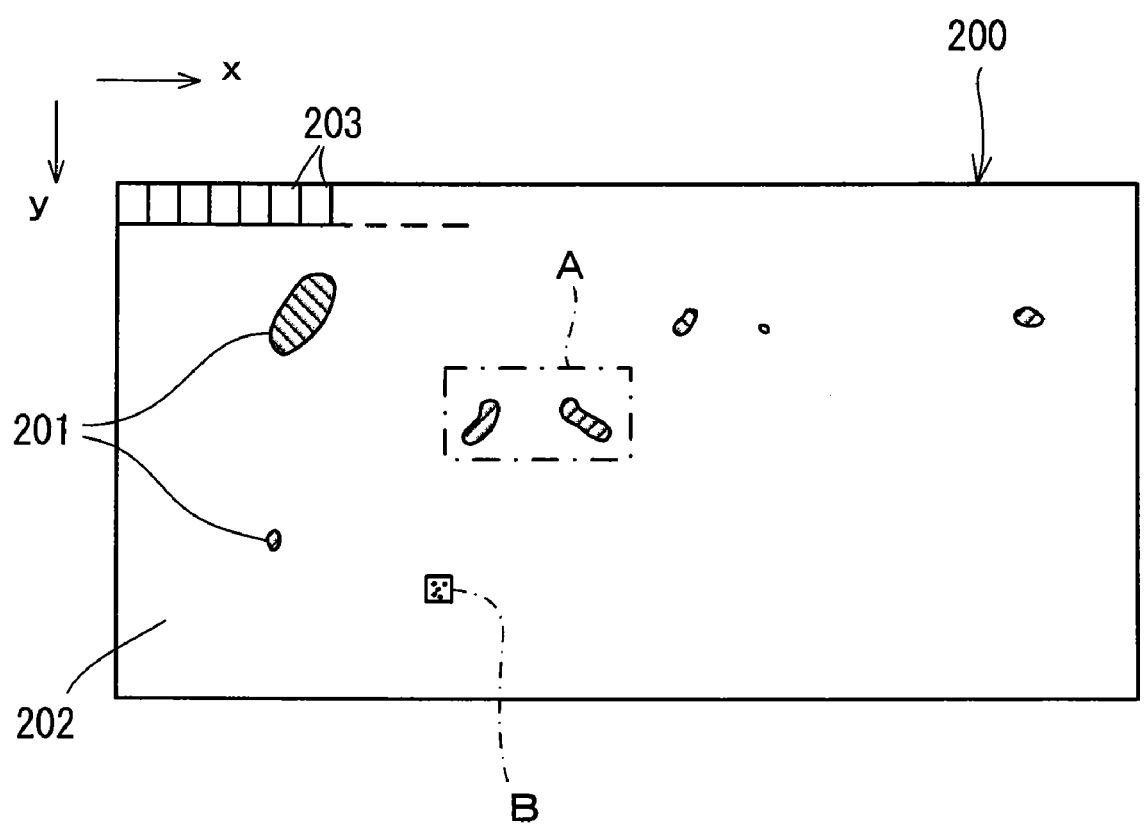
FIG. 2 is a view showing an example of a two-dimensional image of the inner circumferential surface generated in the surface inspection apparatus of FIG. 1.

The arithmetic processing unit 60, which receives the reflection light signal from the signal processing unit 62, stores the acquired signal in the storage unit 65. Furthermore, the arithmetic processing unit 60 generates a two-dimensional image of expanding the inner circumferential surface 100a of the inspection object 100 in a planar manner by utilizing the reflection light signal stored in the storage unit 65. FIG. 2 shows an example of the two-dimensional image. The two-dimensional image 200 corresponds to an image of expanding the inner circumferential surface 100a on the plain surface defined in the two-dimensional rectangular coordinates system, where the direction of the x-axis is the circumference direction of the inspection object 100 and the direction of the y-axis is the axial direction of the inspection head 16. In the two-dimensional image 200, convexo-concave parts of defects or the like existing on the inner circumferential surface 100a is represented as a dark part 201, and the normal part of the inner circumferential surface 100a is represented as a bright part 202. When the inspection object 100 is a casting, the image of defects, such as a blow hole or scratches in cutting process, existing on the inner circumferential surface 100*a* is taken as the dark part 201. The arithmetic processing unit 60 inspects the obtained two-dimensional image 200, and discriminates the dark part 201, where specific conditions are fulfilled, as defects. In the following, the detailed procedure of detecting defects will be described with reference to FIG. 3.

Figure 3:
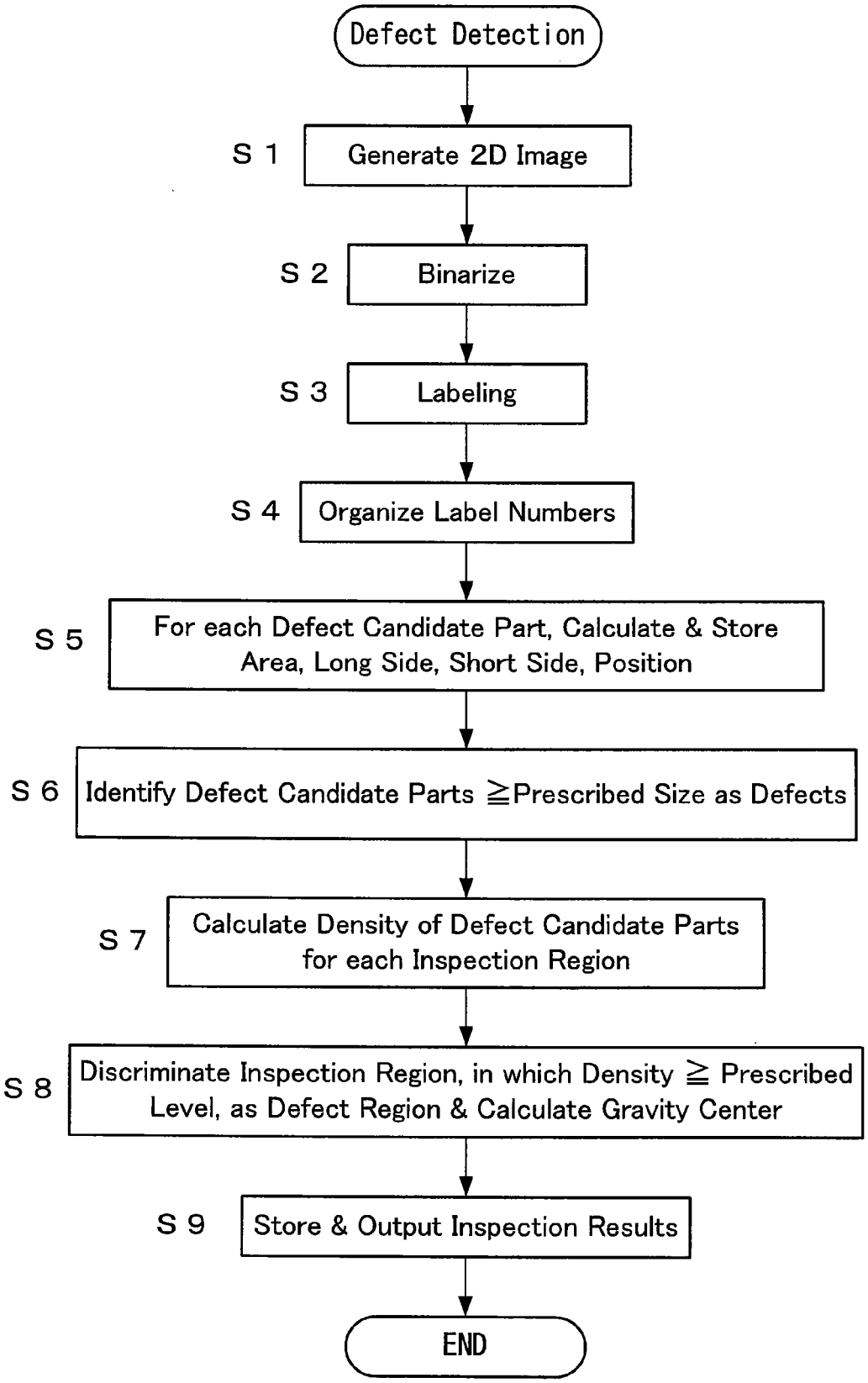
FIG. 3 is a view showing the defect detecting routine executed by the arithmetic processing unit of the surface inspection apparatus of FIG. 1.

FIG. 3 shows a defect detecting routine executed by the arithmetic processing unit 60 to detect defects in the inspection object 100. In the routine of FIG. 3, the arithmetic processing unit 60 first at the step S1 generates a two-dimensional image 200 of the inner circumferential surface 100*a* on the basis of the reflection light signal received from the signal processing unit 62. It is noted that the two-dimensional image 200 is an image generated virtually in RAM of the arithmetic processing unit 60. The size of a single pixel 203 of the two-dimensional image 200 may be arbitrary, but as an example, the pixel is 150 μm in the direction of the x-axis and 50 μm in the direction of the y-axis.

Figure 4:
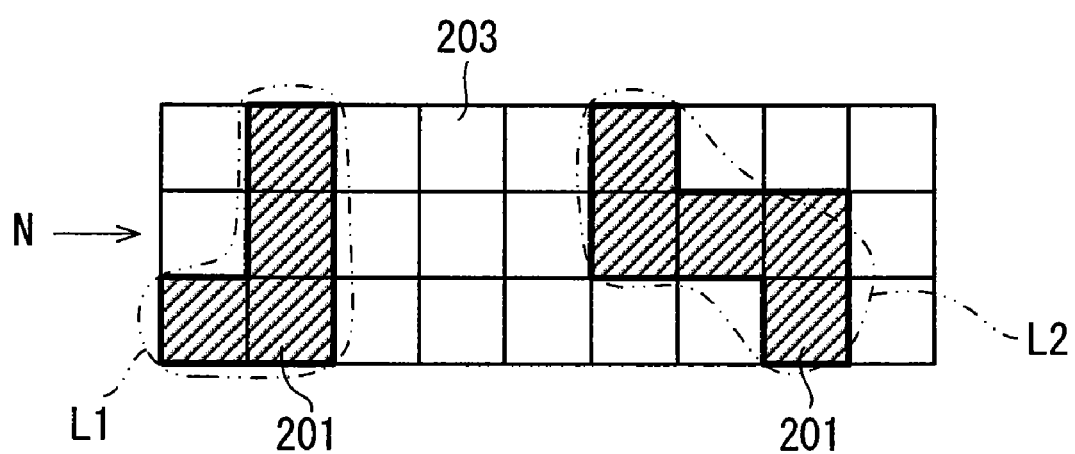
FIG. 4 is a view showing the A-region in FIG. 2 in an enlarged manner.

At the subsequent step S2, the arithmetic processing unit 60 compares the tones of the pixels 203 constituting the two-dimensional image 200 with a prescribed threshold level, and binarizes the two-dimensional image 200 by setting the tone of the darker pixel than the threshold level to 1 and the tone of the brighter pixel to 0. In this way, the tones of the pixels corresponding to the dark region 201 of the two-dimensional image 200 of FIG. 2 are converted to 1, and the tone of the other pixels are converted to 0, respectively. FIG. 4 shows an image of binarizing the A-part of FIG. 2. In FIG. 4, the pixel 203 having a tone of 1 is shown with hatching. It is note that the shapes of asperities or the like existing on the inner circumferential surface 100*a* of the inspection object 100 are shown by the imaginary lines L1, L2, in addition. In FIG. 4, the group of pixels with a tone of 1 (the group of pixels with hatching) corresponds to the first group of pixels having tones corresponding to the defects on the inner circumferential surface 100*a* of the inspection object 100, and the group of pixels with a tone of 0 corresponds to the second group of pixels having tones not corresponding to the defects.

Figure 5:
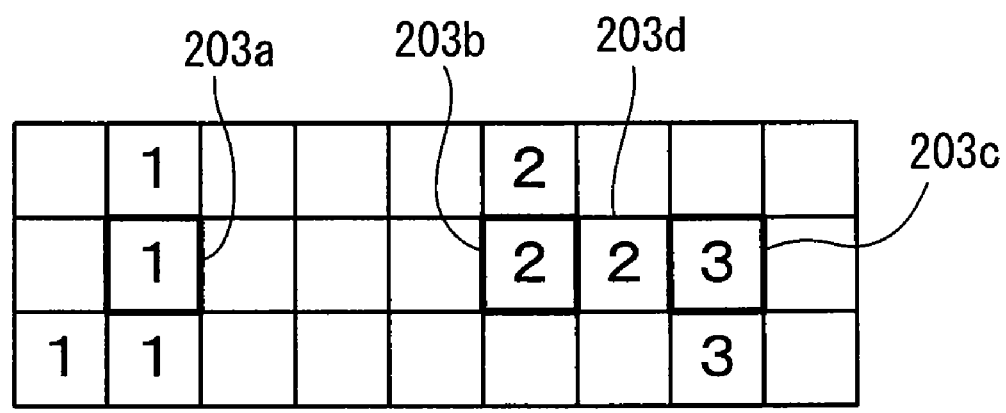
FIG. 5 is a view showing a state in which the labeling process is performed on the image of FIG. 4.

Retuning to FIG. 3, after binarizing the image, the arithmetic processing unit 60 advances to the step S3, and performs a labeling process on the binarized image. The labeling process is a commonly-known process of adding a group attribute to a pixel contained in a two-dimensional image. The labeling process is performed for all the pixels constituting the two-dimensional image, however; the labeling process will be described in the following by illustrating the binarized image of FIG. 4 corresponding to the A-part in FIG. 2. In the labeling process, the tone of each pixel of the binarized image is inspected sequentially in a specific direction. Then, when there exists a pixel having a tone of 1 but having not yet labeled, the pixel is detected as a pixel of interest. For example, when a pixel line N at the middle row in FIG. 4 is scanned in the right direction in the drawing, the pixel 203*a* represented by a bold line in FIG. 5 is detected first as A pixel of interest. After the pixel of interest 203*a* is detected, it is then checked whether the tone of a prescribed number of pixels (four or eight pixels, in general) adjacent to the pixel of interest 203*a* is 0 to 1. Then, a unique label number not used on the binarized image is added to the pixel of interest 203*a* and the pixels continuing thereto and having a tone of 1. In FIG. 5, the label number 1 is added to the pixel of interest 203*a* and the pixels continuing thereto and having a tone of 1. The arithmetic processing unit 60 repeats the above process every time a pixel of interest is detected. In the example of FIG. 5, the pixel of interests 203*b*, 203*c* are detected successively, the label number 2 is added to the pixel of interest 203*b* and the adjacent pixels having a tone of 1, and the label number 3 is added to the pixel of interest 203*c* and the adjacent pixels having a tone of 1, respectively. It is note that since the label number 2 is added to the pixel 203*d* at the right side of the pixel of interest 203*b* at the time of inspecting the pixel of interest 203*b*, the pixel 203*d* is not detected as a pixel of interest. Moreover, since the label number 2 has already been added to the pixel 203*d* at the time of inspecting the pixel of interest 203*c*, the label number 3 is not added to. The labeling process is repeated until no pixel of interest is detected on the binarized image, thereafter, the labeling process is ended.

Figure 6:
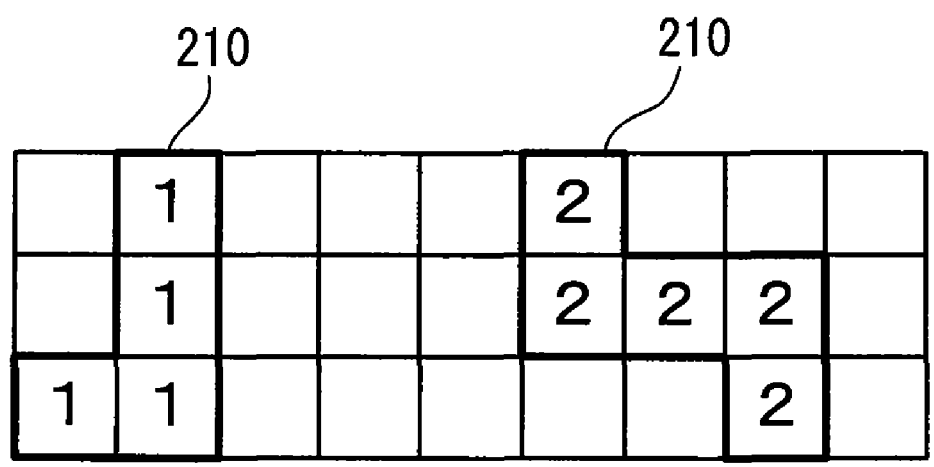
FIG. 6 is a view showing a state in which the label numbers added to the pixels of FIG. 5 are organized.

Returning to FIG. 3, after the labeling process is ended, the arithmetic processing unit 60 then advances to the step S4, and organizes the label numbers. In the organization of the label numbers, parts where different label numbers are added to the adjacent pixels are detected, and the label numbers are organized in such a manner that the adjacent pixels have the same label numbers. In the example of FIG. 5, although the pixels 203*c*, 203*d* are adjacent to each other, the label numbers 2, 3 are added thereto. Thus, in order to resolve this, the label number of all the pixels 203*c*, 203*e* with the label number 3 is changed to 2. FIG. 6 shows the state after the label change. In FIG. 6, the group of pixels with the same label number is represented in a surrounded manner with a bold line. As is apparent from the comparison between FIG. 4 and FIG. 6, all the pixels to which a tone of 1 is given corresponding to the left dark part 201 is grouped by adding the label number 1, and all the pixels to which a tone of 1 is added corresponding to the right dark part 201 is grouped by adding the label number 2. The pixels grouped in this way are a first group of pixels having a tone corresponding to the defects on the inner circumferential surface 100*a* of the inspection object 100, and furthermore correspond to a defect candidate part 210 extracted for every region surrounded by the second group of pixels having tones not corresponding to the defects. It is note that the minimum unit of the defect candidate part 210 is a pixel. Namely, when the tone of the single pixel 203 is 1 and the tones of the surrounding pixels 203 are all 0, the pixel by itself having a tone of 1 is treated as a defect candidate part 210. The defect candidate part 210 obtained in this way corresponds to the dark part 201 in the two-dimensional image shown in FIG. 2.

Furthermore, in the organizing of the label numbers, the label numbers of each group are organized in the descending order of the number of pixels. In the example of FIG. 6, since the right group of pixels includes more pixels than the left group of pixels, the label number of the right group of pixels is replace with 1, and the label number of the left group of pixels is replaced with 2. It is note that a case that two dark parts 201 exist is illustrated in FIG. 4 to FIG. 7, but the organization of the label numbers is performed over the whole region of the binarized image. Accordingly, the label numbers illustrated in FIG. 6 and FIG. 7 do not necessarily coincide with the process results for the entire two-dimensional image of FIG. 2.

Returning to FIG. 3, after the organization of the label numbers is ended, the arithmetic processing unit 60 calculates areas, lengths of long side and short side, positions on the two-dimensional image for all the defect candidate parts 210 extracted in the processes of the step S3 and S4, and stores the calculation results in RAM or the storage unit 65 of the arithmetic processing unit 60. The area may be represented by the number of pixels contained in the defect candidate part 210, or the real area of the defect candidate part 210 may be obtained by the product of the area occupied by a pixel and the number of pixels. The lengths of the long side and short side of the defect candidate part 210 can be obtained from the product of the number of pixels in the direction of the x-axis and in the direction of the y-axis occupied by the defect candidate part 210 and the real sizes per a pixel. For example, the position of the defect candidate part 210 may be represented by the x-coordinate and y-coordinate of a position which represents the defect candidate part 210 (the position of the gravity center, as an example).

At the subsequent step S6, the arithmetic processing unit 60 detects defect candidate parts 210 larger than a prescribed size, and identifies all of these defect candidate parts 210 as defects. For example, the defect candidate part 210 whose short side is equal to or longer than 0.2 mm is identified as a defect. Furthermore, at the next step S7, the arithmetic processing unit 60 inspects the density of the defect candidate parts 210, each of which is not treated as a defect at the step S6 (namely, the defect candidate parts 210, each of which is smaller than the prescribed size) for each of the prescribed inspection regions on the two-dimensional image. When the miniature dark regions 201, each of which is not discriminated as a defect at the step S6, are concentrated in a certain region, these might be recognized as a defect in view of a person for inspection. So, this process is a process of identifying the region where such miniature dark regions 201 are closely concentrated as a defect region.

Figure 8:
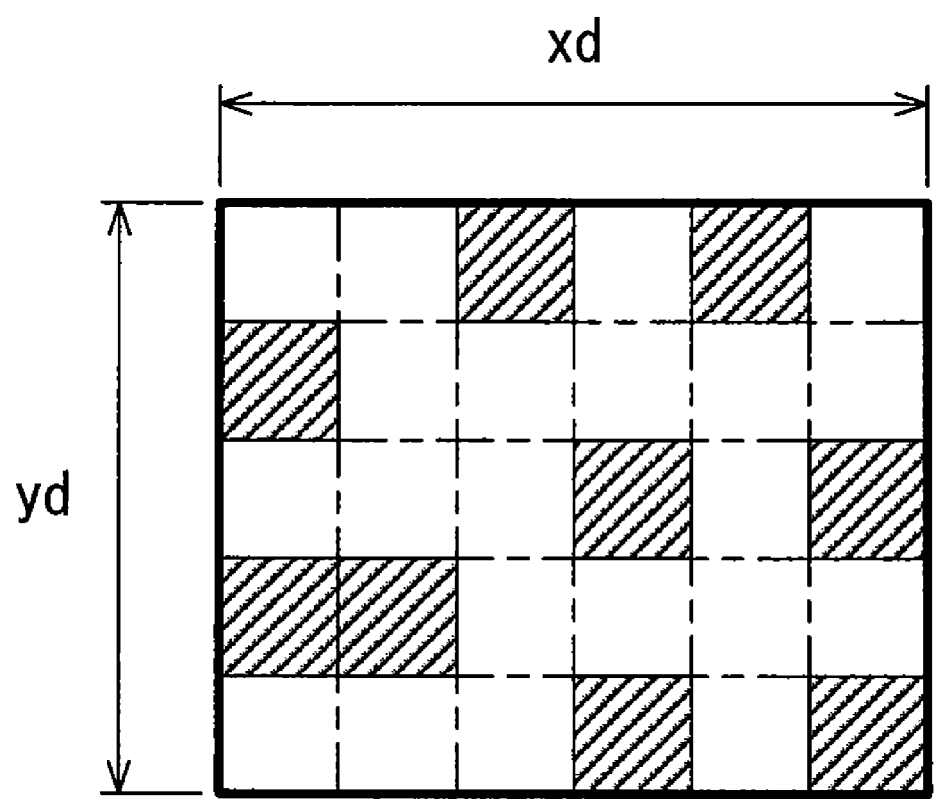
FIG. 8 is a view showing the B-part in FIG. 2 in an enlarged manner.

In the process of the step S7, an inspection region B having a prescribed size is set in the two-dimensional image as shown in FIG. 2, and the density of the defect candidate parts 210 is inspected for each inspection region B. FIG. 8 is an enlarged view of the inspection region B of FIG. 2. The dimensions xd, yd of the inspection region B in the direction of the x-axis and in the direction of the y-axis may be set arbitrarily. In the inspection region B of FIG. 8, the miniature defect candidate parts 210, each of which alone is smaller than a defect, are concentrated in a relatively close region. Since the arithmetic processing unit 60 identifies such a region as a defect region, the number of the defect candidate parts 210 existing in the inspection region B and having an area equal to or larger than the prescribed area is discriminated at the step S7 on the basis of the information obtained at the step S5, such as the area of the defect candidate part 210; and the density of the defect candidate parts 210 in the inspection region B is discriminated by way of the number.

Figure 9:
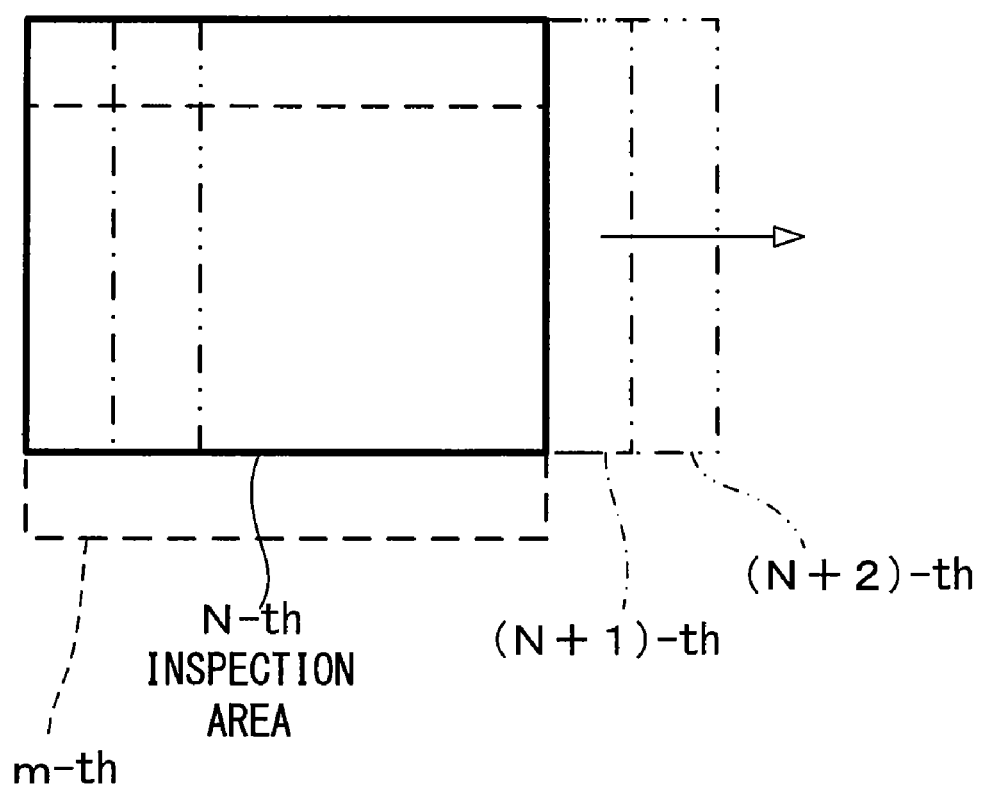
FIG. 9 is a view showing a state in which the inspection region is shifted.

At the subsequent step S8, the arithmetic processing unit 60 identifies the inspection region B where the density of the defect candidate parts 210 is equal to or more than a prescribed level as a defect region. For example, when equal to or more than the prescribed number of the defect candidate parts 210 having an area equal to or larger than the prescribed area exist, their density is recognized high, and the inspection region B is identified as a defect region. Furthermore, when identified as a defect region at the step S8, the position of the gravity center of the group of the miniature defect candidate parts 210 contained in the region is calculated as a position representing these defect candidate parts 210. It is note that the inspection region B is set on the two-dimensional image as shown FIG. 9, by sequentially changing a position thereof in a partially overlapped manner in the direction of the x-axis. When the inspection region B has gone around the inner circumferential surface 100a in the direction of the x-axis, the inspection region B is shifted in a partially overlapped manner in the direction of the y-axis. Hereinafter, the set of the inspection region B and the inspection of the density in the region are repeated in a similar manner. It is note that the defect candidate part 210 identified as a defects at the step S6 may be or may not be eliminated from the target of inspection in the inspection of the density. Even when not eliminated, the region where only the miniature defect candidate parts 210 not identified as defects at the step S6 are concentrated can be identified as a defect region.

Return to FIG. 3, after finishing the identification of the defect region at the step S8, the arithmetic processing unit 60 advances to the step S9, stores the identifying results at the steps S6 and S8 as the inspection results in the storage unit 65, and outputs them to the output unit 64. With regard to the output to the output unit 64, the defects identified at the step S6 and the defects identified at the step S8 may be presented to a user as defects of a same type without distinguishing them, or they may be presented to the user in a distinguished manner. Even when both are presented to the user in a distinguished manner, the region in which miniature blow holes or the like, each of which alone is not discriminated as a defect, are concentrated can be detected as a semi-defect, and the existence or nonexistence thereof can be informed to the user. Furthermore, by presenting a user with the position of the gravity center of the defect candidate parts 210 calculated at the step S8, the position where miniature asperities or the like that can be regarded as a defect exist can be informed to the user, and can be provided for the confirmation of the inspection results. After the above process is finished, the arithmetic processing unit 60 ends the defect detecting routine. It is note that the correspondence relations shown in FIG. 4 to FIG. 8 between the defect candidate parts and the size of a pixel is for illustrative purpose only, and does not show the situation in a real inspection.

As described above, according to the surface inspection apparatus 1 in this embodiment, the defect candidate part 210 which is equal to or larger than a prescribed size on the two-dimensional image of the inner circumferential surface 100a is identified as a defect; and when the miniature defect candidate parts 210, each of which is smaller than the size and each of which alone is not treated as a defect, are closely concentrated in a relatively close region, the region can be identified as a defect region. In this way, it becomes not necessary to set the threshold level of the size of the defect candidate part 210 more than necessary so as to discriminate it as a defect; and the possibility that miniature and stand-alone defect candidate parts 210 might be excessively detected as defects can be eliminated. On the other hand, the closely concentrated part of the miniature defect candidate parts 210, each of which can be identified as a defect in a visual observation of a user, is not looked over and can be detected as a defect or a semi-defect and be presented the existence or nonexistence thereof to a user.

Moreover, the resolution of the two-dimensional image, in other words, the size of a single pixel may be set in such a manner that the miniature dark region 201, which should be a target of evaluation in the inspection of a defect region, occupies at least a single pixel on the two-dimensional image in the present invention. Thus, it is not necessary to set a tiny resolution of inspection more than necessary. Accordingly, even when the inspection head 16 is rotated at a relatively high speed, defects and the defect regions can be detected with a high precision and the degradation of the inspection efficiency due to setting of a higher definition of resolution can be prevented.

In the above embodiment, the arithmetic processing unit 60 functions as the image generating device by executing the step S1 in FIG. 3, functions as the defect candidate extracting device by executing the steps S2 to S5, functions as the defect identifying device by executing the step S6, and functions as the defect region identifying device by executing the steps S7 and S8.

The present invention is not limited to the above form, can be embodied in various forms. For example, in the above embodiment, the inner circumferential surface is scanned with an inspection light by driving out the inspection head in the axial direction while rotating it. However, the present invention can be applied even to a surface inspection apparatus in which at least one of the rotary motion or the linear motion of the inspection head is omitted and the surface of the inspection object is scanned by rotary moving or linearly moving the inspection object instead of the omitted motion. The process of distinguishing from the two-dimensional image the first pixel having tones corresponding to defects and the second pixel having the other tones is not limited to an example of binarizing an image for classification. The pixel corresponding to defects may be distinguished by using a grayscale image or a color image. The process of extracting the defect candidate parts is also not limited to the labeling process, and various image processing methods may be used.

In the above embodiment, the density of the defect candidate parts in an inspection region is discriminated by using the number of defect candidate parts larger than the prescribed area, however; the density may be discriminated by a ratio of the total area defect candidate parts occupying the area of the inspection region. Alternatively, the discrimination of the density can be performed by using various information, for example by paying attention to one of the miniature defect candidate parts, each of which alone is not identified as a defect, and discriminating the density with reference to the distance between the defect candidate part to which attention is paid and the adjacent defect candidate part.

Figure 10:
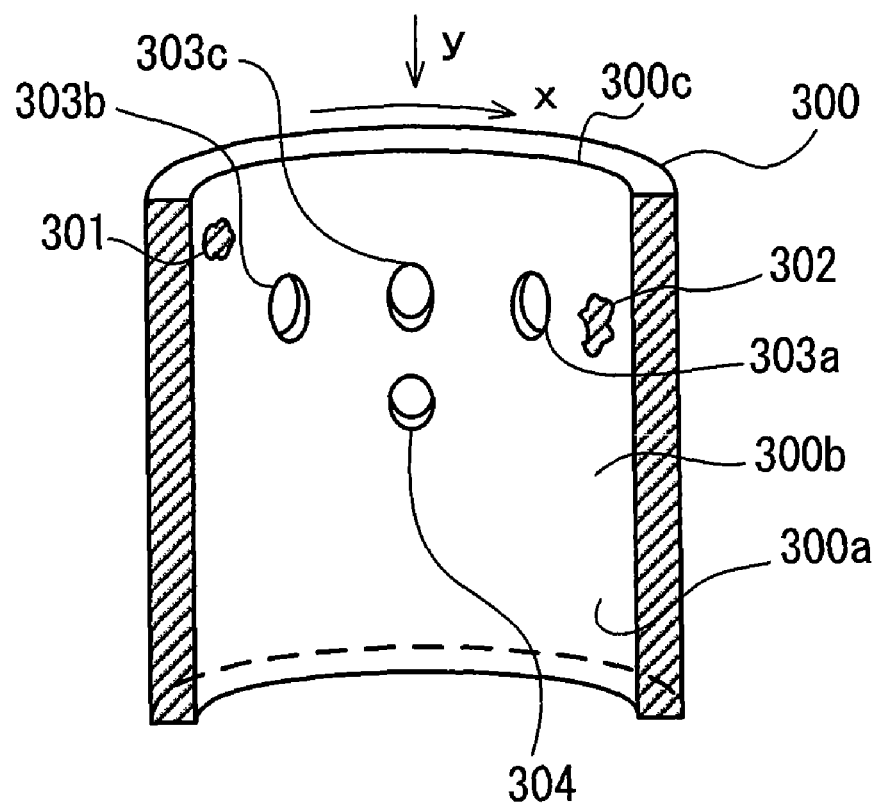
FIG. 10 is a partially cut-away perspective view showing an inspection object.

Next, a surface inspection apparatus in another embodiment of the present invention will be described. The structure of the surface inspection apparatus in this embodiment is same as the structure illustrated in FIG. 1, and thus their description will be omitted. The present embodiment differs from the above embodiment in the processes by the arithmetic processing unit 60. This will be described in the following. The arithmetic processing unit 60 serving as the image generating device generates a two-dimensional image of expanding the inner circumferential surface 300a of the inspection object 300 shown in FIG. 10 in a planar manner by utilizing the reflection light signal stored in the storage unit 65. Namely, the arithmetic processing unit 60 sets x-axis along the circumferential direction of the inspection object 300 and sets y-axis along the axial direction, respectively as shown in FIG. 10, and generates a two-dimensional image of expanding the inner circumferential surface 300a on the plain surface defined in the two-dimensional rectangular coordinates system consisting of the x-axis and the y-axis. The two-dimensional image is an 8-bit grayscale image, for example. The direction of x-axis is a circumference-equivalent direction on the two-dimensional image 400, and the direction of y-axis is an axis-equivalent direction on the two-dimensional image 400.

The defects 301, 302 such as blow holes and the processed holes 303a, 303b, 303c, 304 serving as the processed parts exist on the inner circumferential surface 300a of the inspection object 300 of FIG. 10 as regions having a lower reflectivity than the texture 300b. The texture 300b is a cutting work surface without defects. The processed holes 303a to 303c have a same shape and a same size, and the positions of these holes 303a to 303c in the direction of the y-axis are also the same. In the following, when it is not necessary to distinguish the processed holes 303a to 303c, the will be denoted as processed holes 303. The processed hole 304 differs from the processed hole 303 in its shape and size, and is shifted in the direction of the y-axis from the processed hole 303.

Figure 11:
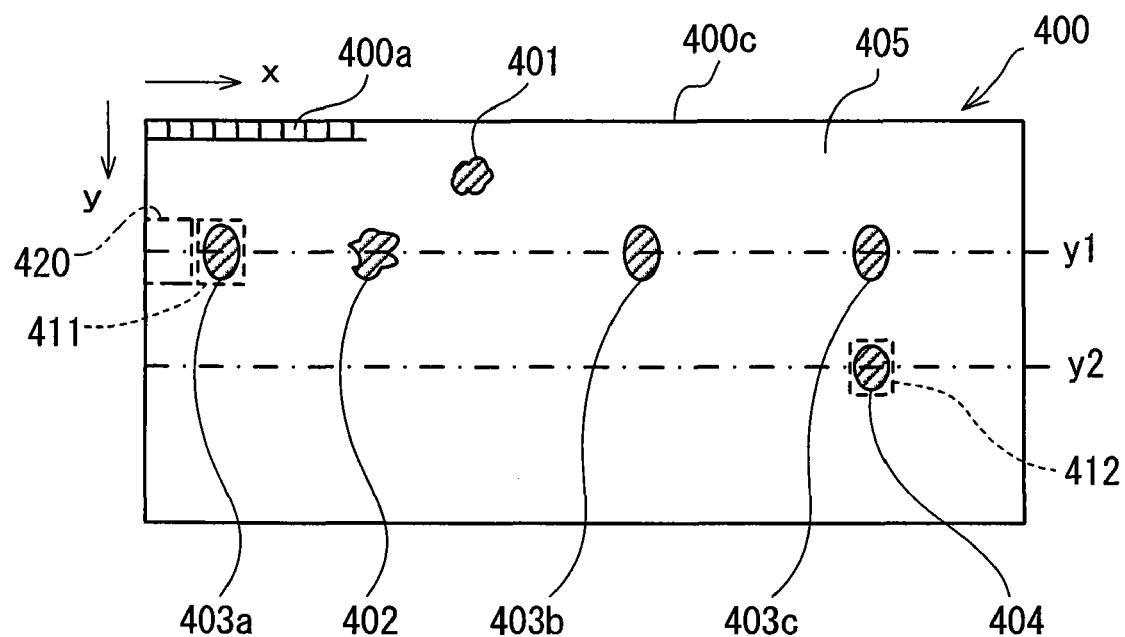
FIG. 11 is a view showing another example of the two-dimensional image of the inner circumferential surface generated by the surface inspection apparatus of FIG. 1.

FIG. 11 shows an example of the two-dimensional image generated by the arithmetic processing unit 60 corresponding to the inner circumferential surface 300a of FIG. 10. The two-dimensional image 400 is formed by arranging a lot of pixels 400a in the direction of the x-axis and in the direction of the y-axis. The size occupied by a single pixel 400a on the inner circumferential surface 300a may be arbitrary, but as an example, the width of the single pixel 400a in the direction of the x-axis corresponds to 150 μm on the inner circumferential surface 300a, the width thereof in the direction of the y-axis corresponds to 50 μm on the inner circumferential surface 300a. the defect images 401, 402 corresponding to the defects 301, 302 and the processed hole image 403a to 403c (they may be represented by the reference symbol 403.), 404 corresponding to the processed holes 303a to 303c, 304 appear on the two-dimensional image 400. The density Values of these images are darker (lower) than that of the background region 405 corresponding to the texture 300b of the inner circumferential surface 300a. Namely in this embodiment, the density value of the pixel 400a in the two-dimensional image 400 gets larger as the amount of the reflection light increases, and defects and processed parts appear as dark regions.

The arithmetic processing unit 60 discriminates whether a defect exists on the inner circumferential surface 300a of the inspection object 300 by processing the two-dimensional image 400 in conformity with a prescribed algorithm, and outputs the discrimination result to the output unit 64. In the defect detection, the existence or nonexistence of a defect image is discriminate by paying attention to the dark part in the two-dimensional image 400. However, in the two-dimensional image 400 of FIG. 11, the processed hole images 403, 404 also appear as the dark parts in a similar manner to the defect images 401, 402. Thus, even if the defects 301, 302 do not exist in the inspection object 300, the processed hole images 403, 404 might be discriminated as defects, and the inspection object 300 might be erroneously determined as a defective product. In order to avoid such an erroneous decision, the arithmetic processing unit 60 eliminates the influence of the processed part such as the processed hole 303, 304 on the defect detection by executing a defect detecting process shown in FIG. 13. The defect detecting process is a process for discriminating the existence or nonexistence of defects, and is performed by preparing the image of the processed part which is already known to exist on the inner circumferential surface 300a of the inspection object 300 as a reference image, detecting the image of the processed part on the basis of the degree of coincidence between the reference image and the image which appears as a dark part on the two-dimensional image 400, and eliminating the image of the detected processed part from the target of defect discrimination.

In case of inspecting the two-dimensional image 400 of FIG. 11, a reference image of extracting only the processed hole images 403 and a reference image of extracting only the processed hole images 404 are prepared, respectively. However, it is assumed here that the images of the rectangle regions 411, 412 that have a minimum size required to enclose the processed hole image 403 or the processed hole image 404 are extracted from the two-dimensional image 400 and are prepared as the reference images. In the following, they may be represented as the reference images 411, 412. Since the processed holes 303a, 303b, 303c have a same shape and a same size, a common, namely a single reference image 411 may be prepared corresponding to them. The reference images 411, 412 can be created by a user's appointing the regions to be used as the reference images 411, 412 in the two-dimensional image 400 that is obtained by actually photographing the inner circumferential surface 300a of the inspection object 300. Alternatively, the reference images 411, 412 may be generated by calculating the images of the processed holes 303, 304 from the design data and the shooting condition of the inspection object 300. It is note that the reference images 411, 412 are generated as grayscale images having the same tones as those of the two-dimensional image 400.

The reference images 411, 412 are stored in the storage unit 65 in advance. FIG. 12 shows an example of the data structure of the reference images 411, 412 stored in the storage unit 65. The data of the reference images 411, 412 are numerical data describing the density value of the pixels contained in the respective reference images 411, 412 in the alignment order of the pixels. These data are stored in the storage unit 65 in a correlated manner with the representative coordinates y1, y2 of the processed hole images 403, 404 corresponding to the reference images 411, 412 in the direction of y-axis and the numbers of them N1, N2. For example, y-coordinates of gravity centers (or the center) of the processed hole images 403, 404 are selected as the representative coordinates y1, y2. As an example, the origin of the coordinate in the direction of y-axis is set at the upper end 400c of the two-dimensional image 400, namely at the edge 300c in the axial direction of the inner circumferential surface 300a of FIG. 10. The numbers N1, N2 are values denoting how many processed holes 303, 304 having a same shape and a same size exist at the representative coordinates y1, y2, respectively. In other words, they are the numbers of the processed hole images 403, 404 corresponding to the reference images 411, 412, that should exist at the position denoted by y-coordinate y1, y2, respectively. In the example of FIG. 11, the number N1 is 3, and the number N2 is 1.

Figure 13:
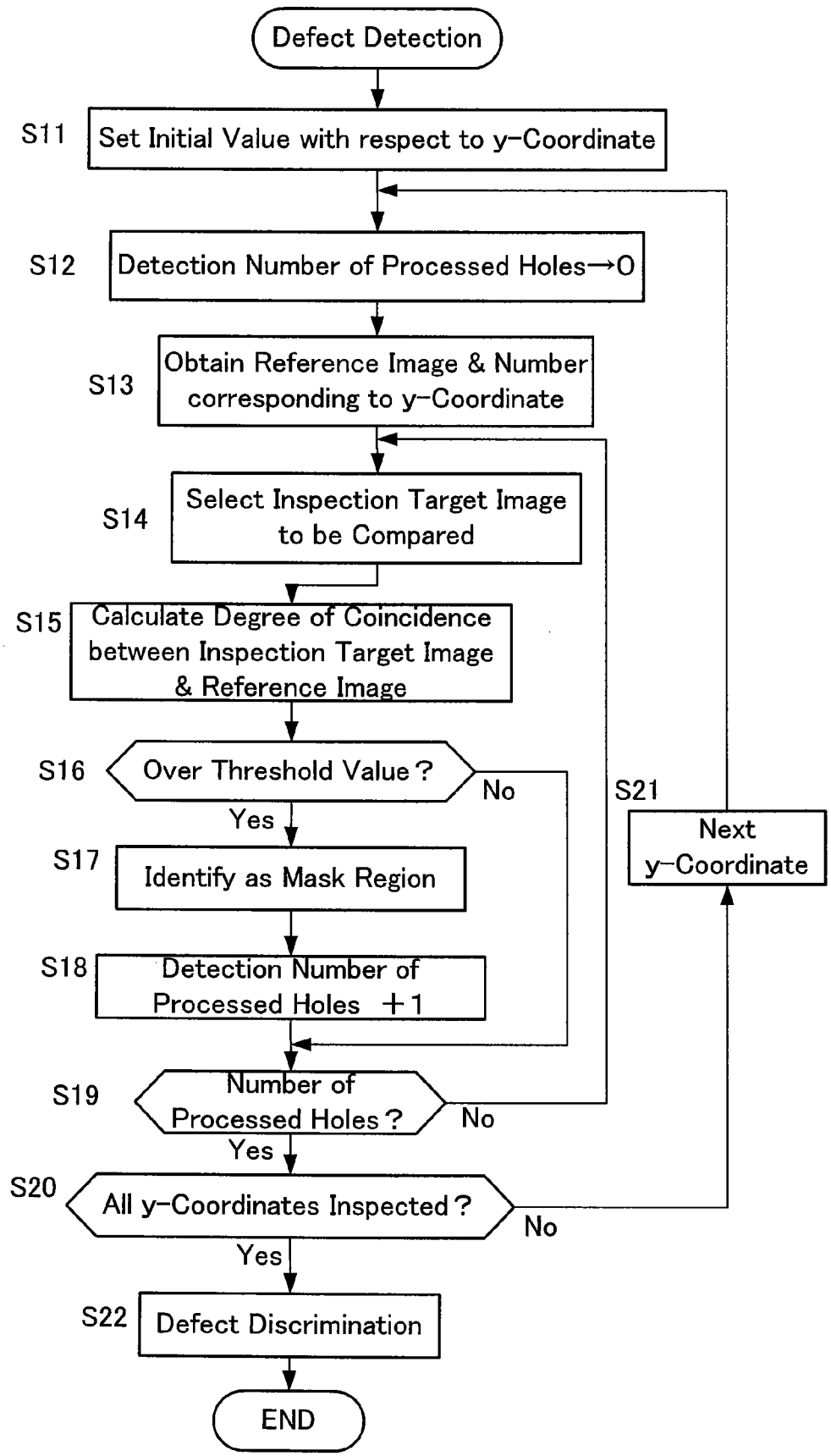
FIG. 13 is a flowchart showing the defect detecting process executed by the arithmetic processing unit of the surface inspection apparatus of FIG. 1.

Next, the defect detecting process of FIG. 13 will be described. When the scanning of the inner circumferential surface 300a is finished, the arithmetic processing unit 60 generates a two-dimensional image 400 of the inner circumferential surface 300a on the basis of the reflection light signal received from the signal processing unit 62. The two-dimensional image 400 is a grayscale image generated virtually in RAM of the arithmetic processing unit 60. After generating the two-dimensional image 400, the arithmetic processing unit 60 starts a defect detecting process, and sets first at the step S11 the initial value with respect to y-coordinate of the target of inspection. In this case, the smallest y-coordinate (y1 in this case) of the representative coordinates y1, y2 correlated with the reference images 411, 412 may be set as the initial value.

At the next step S12, the arithmetic processing unit 60 sets the value of the counter for counting the detection number of the processed holes to the initial value of 0. At the subsequent step S13, the arithmetic processing unit 60 obtains the data of the reference image and the number correlated with y-coordinate of the target of inspection from the storage unit 65. For example, when y-coordinate of the inspection target group of pixels is y1, the arithmetic processing unit 60 obtains the data of the reference image 411 and the number N1 (=3) of the processed holes 303a to 303c.

At the subsequent step S14, the arithmetic processing unit 60 selects the inspection target image to be compared with the reference image from the two-dimensional image 400. For example, when the y-coordinate y1 is set as the target of inspection on the two-dimensional image 400 of FIG. 11, the inspection target image 420 is selected in such a manner that it has a same shape and a same size as the reference image 411 at the y-coordinate y1 and its position in the direction of y-axis coincides with the reference image 411. The position of the inspection target image 420 in the direction of x-axis is changed sequentially in the direction of x-axis by a prescribed number of pixels every time the step S14 is executed. For example, when the step S14 is first executed for the y-coordinate y1, an inspection target image 420 is selected so as to be in contact with the left edge of the two-dimensional image 400, and the position of the inspection target image 420 is changed sequentially toward the right end in the direction of x-axis every time the step S14 is executed. The process corresponds to a process of sequentially changing a position of the reference image 411, on the two-dimensional image 400, within the region in the direction of y-axis, wherein the region has the y-coordinate y1 as its center and has a same dimension as the reference image 411, and from the left end of the two-dimensional image 300 in the direction of x-axis.

At the next step S15, the arithmetic processing unit 60 calculates a degree of coincidence between the inspection target image and the reference image by using the normalized correlation. In a normalized correlation, a positive correlation is shown when the density values have a same tendency between the images to be compared, namely when they are similar, whereas a negative correlation is shown when the density values of both have the opposite tendencies, namely when they are not similar. The correlation equation of a normalized correlation is expressed as: $(A \times 10000)/\sqrt{(B \times C)}$. Here, A denotes the cross-correlation between the inspection target image and the reference image, and is given by $A=N \times \Sigma(I \times T)-(\Sigma I) \times (\Sigma T)$. B denotes the autocorrelation of the inspection target image, and is given by $B=N \times \Sigma(I \times I)-(\Sigma I) \times (\Sigma I)$. C denotes the autocorrelation of the reference image, and is given by $C=N \times \Sigma(T \times T)-(\Sigma T) \times (\Sigma T)$. In the correlation equation, N denotes the number of pixels of the reference image, I denotes the density value of the respective pixel of the inspection target image, and T denotes the density value of the respective pixel of the reference image, respectively.

At the subsequent step S16, the arithmetic processing unit 60 determines whether the normalized correlation value obtained at the step S15 exceeds a prescribed threshold level. A value whose normalized correlation value is regarded to show a positive correlation may be set to the threshold level used here. When beyond the threshold level, the arithmetic processing unit 60 advances to the next step S17, identifies the region extracted as an inspection target image as a mask region, and stores the positions of a group of pixels contained in the mask region on the two-dimensional image 400. At the next step S18, the arithmetic processing unit 60 adds the value of the above counter by 1 and advances to the step S19. On the other hand, when it is determined at the step S16 that the normalized correlation value does not exceed the threshold level, the arithmetic processing unit 60 skips the steps S17, S18 and advances to the step S19.

At the next step S19, the arithmetic processing unit 60 determines whether the above value of the counter (the detection number of the processed holes) coincides with the number of processed holes (N1 at the coordinate y1, for example), which is obtained at the step S13. When the value of the counter does not coincide with the number of processed holes, the arithmetic processing unit 60 retunes to the step S14, and calculates the degree of coincidence between the next inspection target image 420 and the reference image. When the value of the counter coincides with the number of the processed holes at the step S19, the arithmetic processing unit 60 advances to the step S20.

At the step S20, the arithmetic processing unit 60 reference image determines whether the inspection of all the y-coordinates corresponding to the data is ended. Then, when there remain uninspected y-coordinates, the arithmetic processing unit 60 selects the next y-coordinate at the step S21 and returns to the step S12. When the inspection of all the y-coordinates is ended at the step S20, the arithmetic processing unit 60 advances to the next step S22.

At the step S22, the arithmetic processing unit 60 discriminates whether the defect image exist in the two-dimensional image 400 while eliminating the region identified as the mask region from the target of defect discrimination. As an example, the arithmetic processing unit 60 binarizes the two-dimensional image 400 with the threshold level at which the defect images 401, 402 are classified as dark regions, and the background image 405 is classified as a bright region, and discriminates the existence or nonexistence of defects by using the areas or the like of the dark regions in the obtained binary image as a key. In the binarization, all the density values of the pixels identified as the mask region at the step S17 are converted to the same density value as that of the background region 405. In this way, the image regarded as the processed hole image is deleted from the binary image. Accordingly, when only the processed hole image exist on the inner circumferential surface 300a, the probability that the processed hole image might be erroneously discriminated as defects is eliminated. When the defect discrimination is finished for the whole surface of the inner circumferential surface 300a, the arithmetic processing unit 60 ends the defect detecting process of FIG. 13.

In the above processes, the reference images 411, 412 corresponding to the respective processed hole images 403, 404 are prepared in advance. The regions which can be regarded to coincide with the reference images 411, 412 in the two-dimensional image 400 are estimated as the processed hole images, and these are eliminated from the target of defect discrimination. Thus, there are no possibilities that a non-defective product without defects might be erroneously discriminated as a defective product by the influence of the processed hole. Moreover, a separate reference image is prepared for each of the processed hole images 403, 404 having different shapes or sizes, and each of the reference images is stored in a correlated manner with the position (y-coordinate) and the number of the processed hole images, and the degree of coincidence between the inspection target image and the reference image is calculated in the narrowed region with reference to the y-coordinate, which representing each of the reference image. When the inspection target image coincides with the reference image, the region of the inspection target image is identified as a mask region. Thus, regardless of the positions of the processed hole images 403, 404 in the direction of x-axis of the two-dimensional image 400 (equivalent to the circumferential direction of the inspection object 300), the mask region can be specified easily and speedily. This point will be described below.

The edge 400c of the two-dimensional image 400 corresponding to the edge 300c of the inner circumferential surface 300a is selected as a reference in the axial direction of the inspection object 300, and y-coordinates at which the processed hole image 403, 404 exist can be uniquely specified with respect to the reference. However, x-coordinates of the processed hole images 403, 404 can be varied in accordance with the relation between the scanning starting position on the inner circumferential surface 300a of the inspection object 300 and the positions of the processed holes 303, 304. There are no defined references which can be used for specifying the positions of the processed hole image 403, 404 in the direction of x-axis on the two-dimensional image 400. Thus, one might try to mask the processed hole images 403, 404 by storing the processed hole images 403, 404 existing on the whole two-dimensional image 400 in a single mask image and overlapping the mask image on the two-dimensional image 400. However, when the positions of the processed hole images 403, 404 are varied, the masking position is shifted and the processed hole images 403, 404 are detected as defects. Even when, in order to prevent the above, the position of the mask image is varied in the direction of x-axis so as to be aligned with the processed hole images 403, 404, the data amount of a mask image in a size corresponding to the entire inner circumferential surface 300a is large, and it takes long time to positioning process.

On the contrary, in this embodiment, since the reference images 411, 412 are separately prepared for each of the processed hole images 403, 404 having at least different shapes or different sizes, the size of the reference images 411, 412 is small, and their data amount is small. Thus, when the reference images 411, 412 are moved relatively with respect to the two-dimensional image 400 at the y-coordinates y1, y2, it takes short time to process them. Moreover, the region where the reference image 411 should be compared with the inspection image 420 is narrowed to a region in the direction of y-axis, wherein the region has the y-coordinate y1 as its center and has a same dimension as the reference image 411, and the region where the reference image 412 should be compared With the inspection image 420 is narrowed to a region in the direction of y-axis, wherein the region has the y-coordinate y2 as its center and has a same dimension as the reference image 412. Thus, it is not necessary to compare the reference images 411, 412 with the whole surface of the two-dimensional image 400. Accordingly, the mask process for specifying the region to be eliminated from the target of defect inspection can be performed speedily.

Moreover in this embodiment, the numbers N1, N2 of the processed hole images 403, 404 which should exist at the y-coordinates y1, y2 corresponding to the respective reference images 411, 412 are grasped in advance. When just the numbers of mask regions corresponding to the numbers N1, N2 are identified, detection of the mask region at a same y-coordinate is finished (the step S19 to S20). Thus, even when a defect image similar to the processed hole image exists at the same y-coordinates as those of the processed hole images 403, 404, this does not affect the discrimination of the existence or nonexistence of defects. For example, in the two-dimensional image 400 of FIG. 10, three processed hole images 403a to 403c and one defect image 302 exist at y-coordinate of y1. Even if the defect image 302 is discriminated as a mask region in the comparison with the reference image 311, any one of the processed hole images 403 remains not discriminated as a mask region. Thus, the processed hole image 403 is detected as defects in the defect detection at the step S22. In this way, the possibility that the inspection object in which defects exist might be erroneously discriminated as a non-defective product is eliminated.

In the above embodiment, the storage unit 65 corresponds to the reference image storing device. Moreover, the arithmetic processing unit 60 functions as the defect discriminating device by executing the process of FIG. 13, and functions in particular as the eliminating region specifying device by executing the processes of the steps S14 to S19 in FIG. 13.

The present invention is not limited to the above embodiment, and can be embodied in various forms. For example in the above process, the detection of a mask region is finished at the time when the number of times at which the region is identified as a mask region coincides with the number of the processed holes corresponding to the reference images. However, even after the number of the detection of the mask regions coincides with the number of the processed holes, the calculation of the degree of coincidence between the reference image and the inspection target image along the directions of x-axis may be carried on. when more processed hole images are detected than the number corresponding to the reference image, it may be determined that defects exist in the inspection object 300. Further advanced, when more mask regions exist than the number correlated with the reference image, the region having the lowest correlation level value on the basis of the normalized correlation value may be specified as defects. In this way, the number of the processed holes corresponding to the reference image is not only the information for identifying a mask region, but also can be utilized as information for discriminating the existence or nonexistence of defects.

In the above embodiment, y-coordinate of the center is used as the position of the image of the processes hole corresponding to the reference image, however; it is not limited to that, and an appropriate position may be defined as the position of the image of the processes hole.

The means for obtaining a two-dimensional image of the surface of the inspection object is not limited to the above form, and may be modified appropriately. Moreover, the present invention can be applied not only to a case of inspecting the inner circumferential surface but also to a case of inspecting a cylindrical outer circumferential surface. Furthermore, the present invention is not limited to the inspection of an inspection object provided with a processed hole as a processed part, the part processed in any way on the cylindrical surface, which is the target of inspection, may be eliminated from the target of defect discrimination according to the present invention. The concept of processing includes broadly applications of any artificially alternation to the material of an inspection object, for example, may also include various processes such as printing, coloring, surface modification.

The invention claimed is:

1. A surface inspection apparatus, which obtains a two-dimensional image of expanding a cylindrical surface of an inspection object in a planar manner, and discriminates existence or nonexistence of a defect on the surface on the basis of density values of pixels in the two-dimensional image, the surface inspection apparatus comprising:

a reference image storing device which stores images of processed parts to be appeared on the two-dimensional image corresponding to processed parts existing on the surface as separate reference images for each of processed parts which are different in at least shapes or sizes, and stores a position of each image of each processed part in an axis-equivalent direction equivalent to an axial direction of the surface and the number of each of images of a same processed part which should exist in a circumference-equivalent direction equivalent to a circumference direction of the surface in a correlated manner with each of the reference images; and a defect discriminating device which specifies a region to be eliminated from a target of defect discrimination on the two-dimensional image on the basis of each reference image and the position and the number correlated with each reference image, and discriminates the existence or nonexistence of the defect on the basis of the density values of pixels outside the specified region.

2. The surface inspection apparatus according to claim 1, wherein the defect discriminating device comprises an eliminating region specifying device, which narrows a region to be compared with the reference image on the two-dimensional image to a part of the two-dimensional image in the axis-equivalent direction with reference to the position correlated with the reference image, compares density values of pixels of the reference image and of the two-dimensional image in the narrowed region, and specifies the same number of regions as the number correlated with the reference image as regions to be eliminated from the target of defect discrimination on the basis of the comparison result.

3. The surface inspection apparatus according to claim 2, wherein the eliminating region specifying device discriminates a degree of coincidence between the reference image and an inspection target image having the same shape and size as those of the reference image on the two-dimensional image, with sequentially changing a position of the reference image in the narrowed region relatively with respect to the two-dimensional image in the circumference-equivalent direction, and, when the discriminated degree of coincidence exceeds a prescribed threshold level, specifies a region of the inspection target image as a region to be eliminated from the target of defect discrimination.

4. The surface inspection apparatus according to claim 3, wherein the degree of coincidence is calculated by normalized correlation between the reference image and the inspection target image.

5. The surface inspection apparatus according to claim 1, wherein the reference image corresponds to an image obtained by extracting a minimum rectangle region required to enclose an image of a single processed part from the two-dimensional image.

* * * * *